US012029462B2

(12) United States Patent
Brockman et al.

(10) Patent No.: US 12,029,462 B2
(45) Date of Patent: *Jul. 9, 2024

(54) BONE CEMENT DELIVERY SYSTEMS INCLUDING A FLOW DIVERTER AND DROOL ACCUMULATOR

(71) Applicant: Stryker Corporation, Kalamazoo, MI (US)

(72) Inventors: Christopher Scott Brockman, Kalamazoo, MI (US); Gabriel James Harshman, Portage, MI (US)

(73) Assignee: Stryker Corporation, Kalamazoo, MI (US)

( * ) Notice: Subject to any disclaimer, the term of this patent is extended or adjusted under 35 U.S.C. 154(b) by 416 days.

This patent is subject to a terminal disclaimer.

(21) Appl. No.: 17/386,016

(22) Filed: Jul. 27, 2021

(65) Prior Publication Data
US 2021/0353347 A1   Nov. 18, 2021

Related U.S. Application Data

(63) Continuation of application No. 16/487,615, filed as application No. PCT/US2018/019211 on Feb. 22, 2018, now Pat. No. 11,129,659.
(Continued)

(51) Int. Cl.
*A61B 17/88* (2006.01)
*A61M 39/22* (2006.01)
(Continued)

(52) U.S. Cl.
CPC ...... *A61B 17/8827* (2013.01); *A61B 17/8811* (2013.01); *A61B 17/8816* (2013.01);
(Continued)

(58) Field of Classification Search
CPC .................................. A61B 17/8802–17/8847
See application file for complete search history.

(56) References Cited

U.S. PATENT DOCUMENTS 5,356,382 A * 10/1994 Picha ................. A61B 17/3415
606/198
5,567,122 A  10/1996 Schulte
(Continued)

FOREIGN PATENT DOCUMENTS

EP           2022426 A2    2/2009
WO       2008045329 A2    4/2008
(Continued)

OTHER PUBLICATIONS

International Search Report for Application No. PCT/US2018/019211 dated Jun. 11, 2018, 5 pages.

*Primary Examiner* — Zade Coley
(74) *Attorney, Agent, or Firm* — Howard & Howard Attorneys PLLC

(57) ABSTRACT

A system including a flow diverter for delivering bone cement. A cannula coupler is coupled to the flow diverter and configured to be coupled to a delivery cannula. A drool accumulator is coupled to the flow diverter. A user input mechanism is coupled to the flow diverter and configured to actuate a valve and establish fluid communication between the cement reservoir and one of the cannula coupler and the drool accumulator. The fluid communication may be interrupted between the cement reservoir and the other one of the cannula coupler and the drool accumulator. A cement delivery input mechanism may be coupled to the cement reservoir and configured to be actuated to direct the bone cement from the cement reservoir towards the flow diverter. An actuator may be coupled to the drool accumulator and configured to direct the bone cement received in the drool volume towards the flow diverter.

20 Claims, 13 Drawing Sheets

Related U.S. Application Data

(60) Provisional application No. 62/462,043, filed on Feb. 22, 2017.

(51) Int. Cl.
*A61B 17/56* (2006.01)
*A61B 90/00* (2016.01)

(52) U.S. Cl.
CPC ....... *A61B 17/8822* (2013.01); *A61M 39/223* (2013.01); *A61B 2017/564* (2013.01); *A61B 2017/8813* (2013.01); *A61B 2090/0807* (2016.02); *A61M 2039/226* (2013.01)

(56) References Cited

U.S. PATENT DOCUMENTS

| | | | |
|---|---|---|---|
| 5,695,720 A | 12/1997 | Wade et al. | |
| 6,547,432 B2 | 4/2003 | Coffeen et al. | |
| 6,736,537 B2 | 5/2004 | Coffeen et al. | |
| 7,134,782 B2 | 11/2006 | Coffeen et al. | |
| 7,306,361 B2 | 12/2007 | Coffeen et al. | |
| 7,320,540 B2 | 1/2008 | Coffeen | |
| 7,658,537 B2 * | 2/2010 | Coffeen | A61B 17/8822 366/195 |
| 8,226,657 B2 | 7/2012 | Linderman et al. | |
| 8,361,078 B2 | 1/2013 | Beyar et al. | |
| 8,771,278 B2 | 7/2014 | Linderman et al. | |
| 8,876,833 B2 * | 11/2014 | Donovan | A61B 17/8827 606/92 |
| 8,894,658 B2 | 11/2014 | Linderman et al. | |
| 9,095,393 B2 | 8/2015 | Schaus et al. | |
| 9,158,078 B2 | 10/2015 | Toyohara et al. | |
| 9,526,551 B2 | 12/2016 | Linderman et al. | |
| 9,532,823 B2 | 1/2017 | Harshman et al. | |
| 9,655,663 B2 | 5/2017 | Donovan et al. | |
| 9,839,443 B2 | 12/2017 | Brockman et al. | |
| 2005/0180806 A1 * | 8/2005 | Green | A61B 17/8822 401/119 |
| 2007/0039866 A1 | 2/2007 | Schroeder et al. | |
| 2009/0257306 A1 * | 10/2009 | Coffeen | B01F 35/562 366/195 |
| 2010/0274080 A1 * | 10/2010 | Donovan | A61B 17/8855 606/93 |
| 2011/0270181 A1 * | 11/2011 | Donovan | A61B 17/8827 604/150 |
| 2016/0045241 A1 | 2/2016 | Boboltz | |
| 2020/0060741 A1 | 2/2020 | Brockman et al. | |

FOREIGN PATENT DOCUMENTS

| | | | |
|---|---|---|---|
| WO | 2011054110 A1 | 5/2011 | |
| WO | 2012094549 A1 | 7/2012 | |

* cited by examiner

FIG. 9
FIG. 10
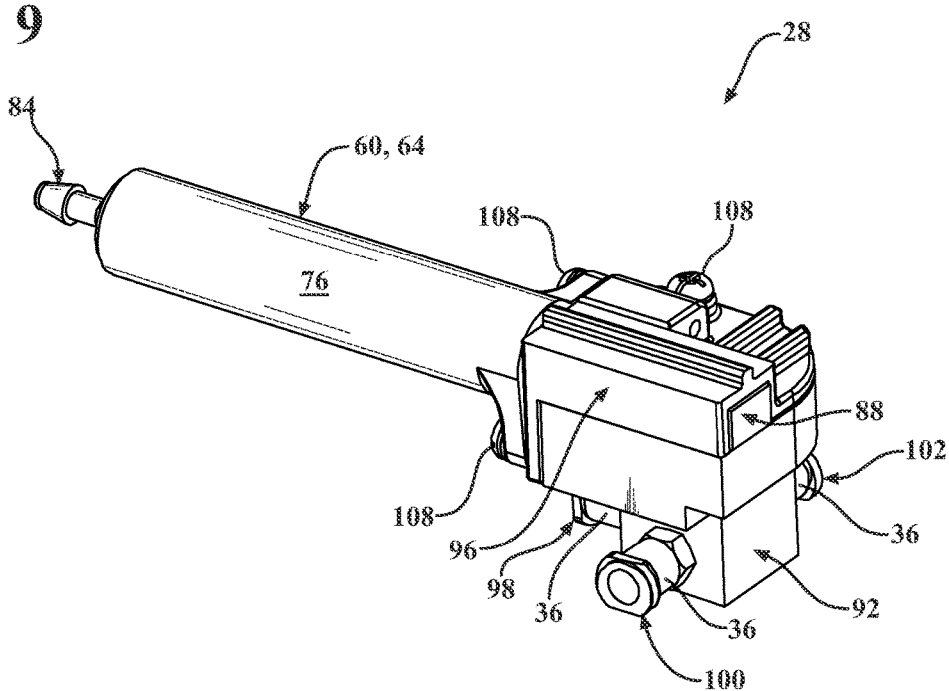
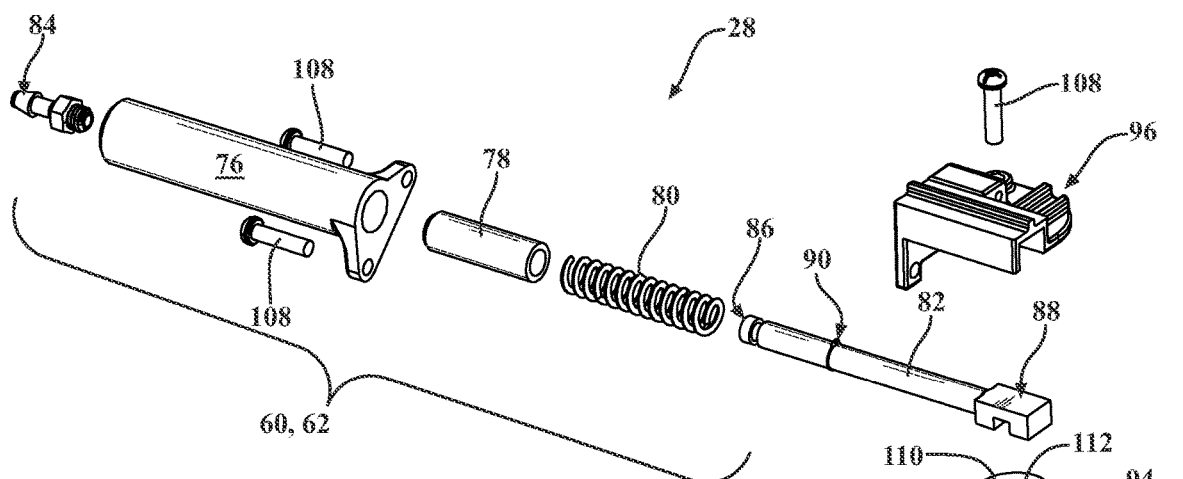
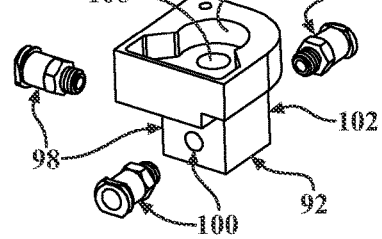

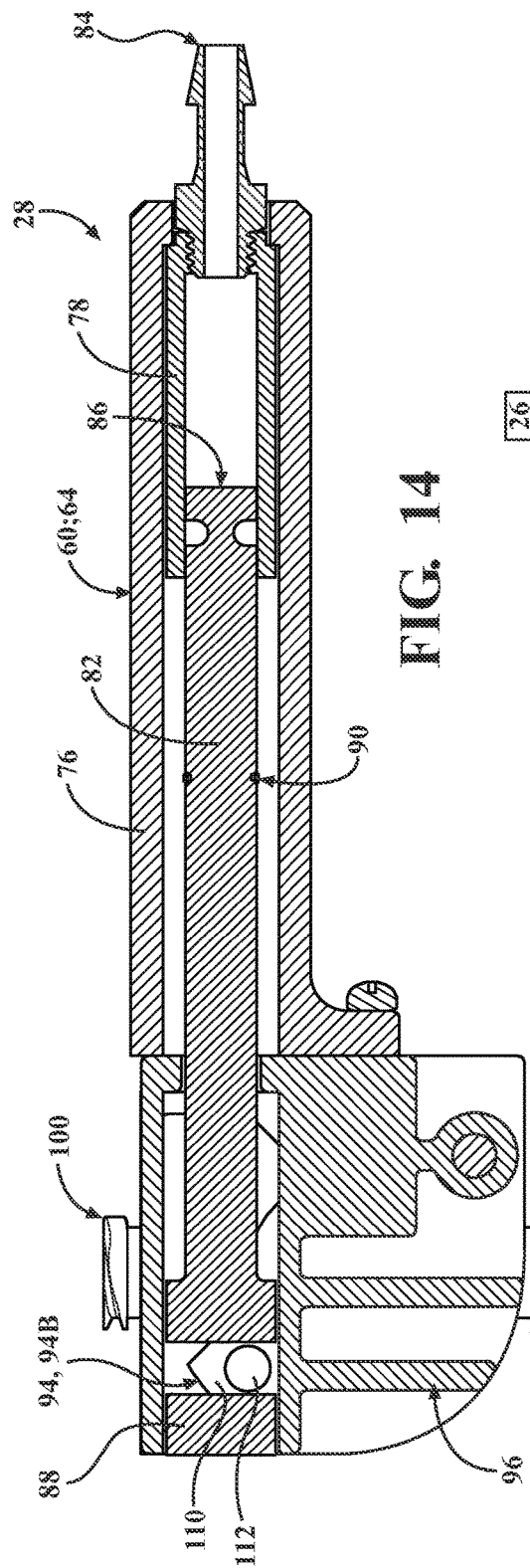
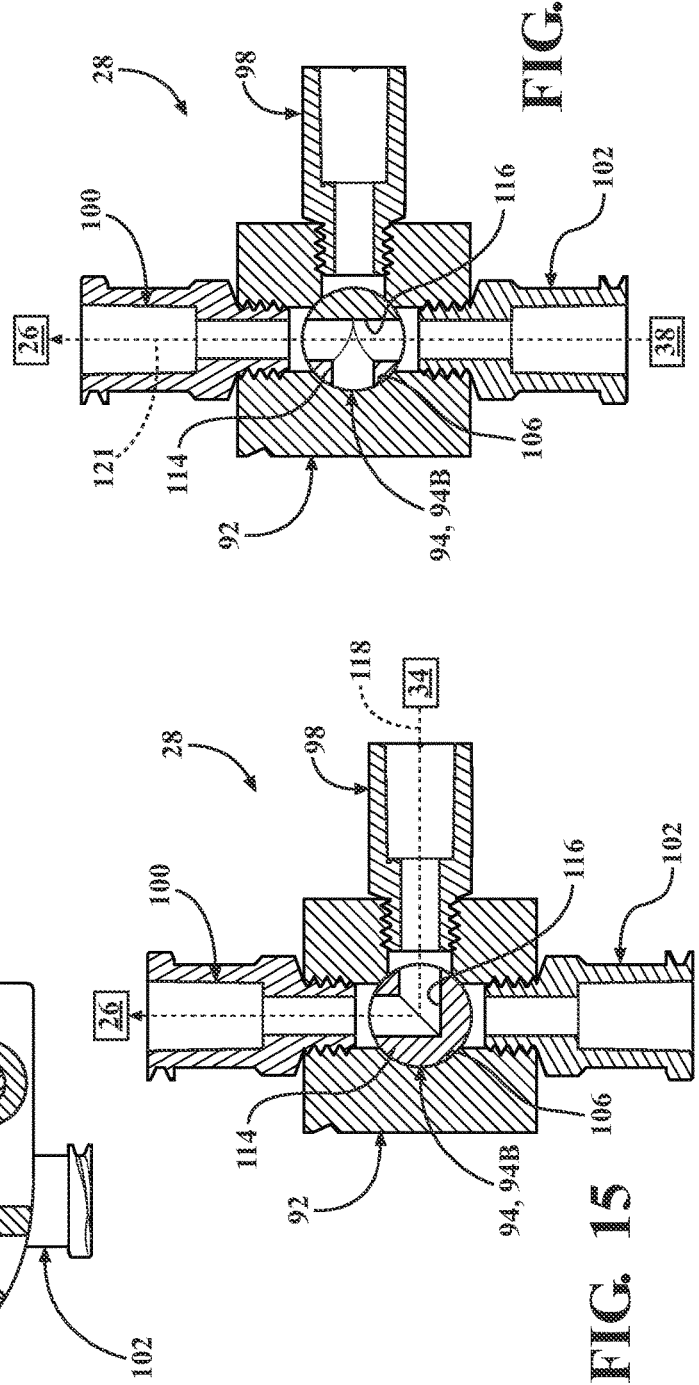

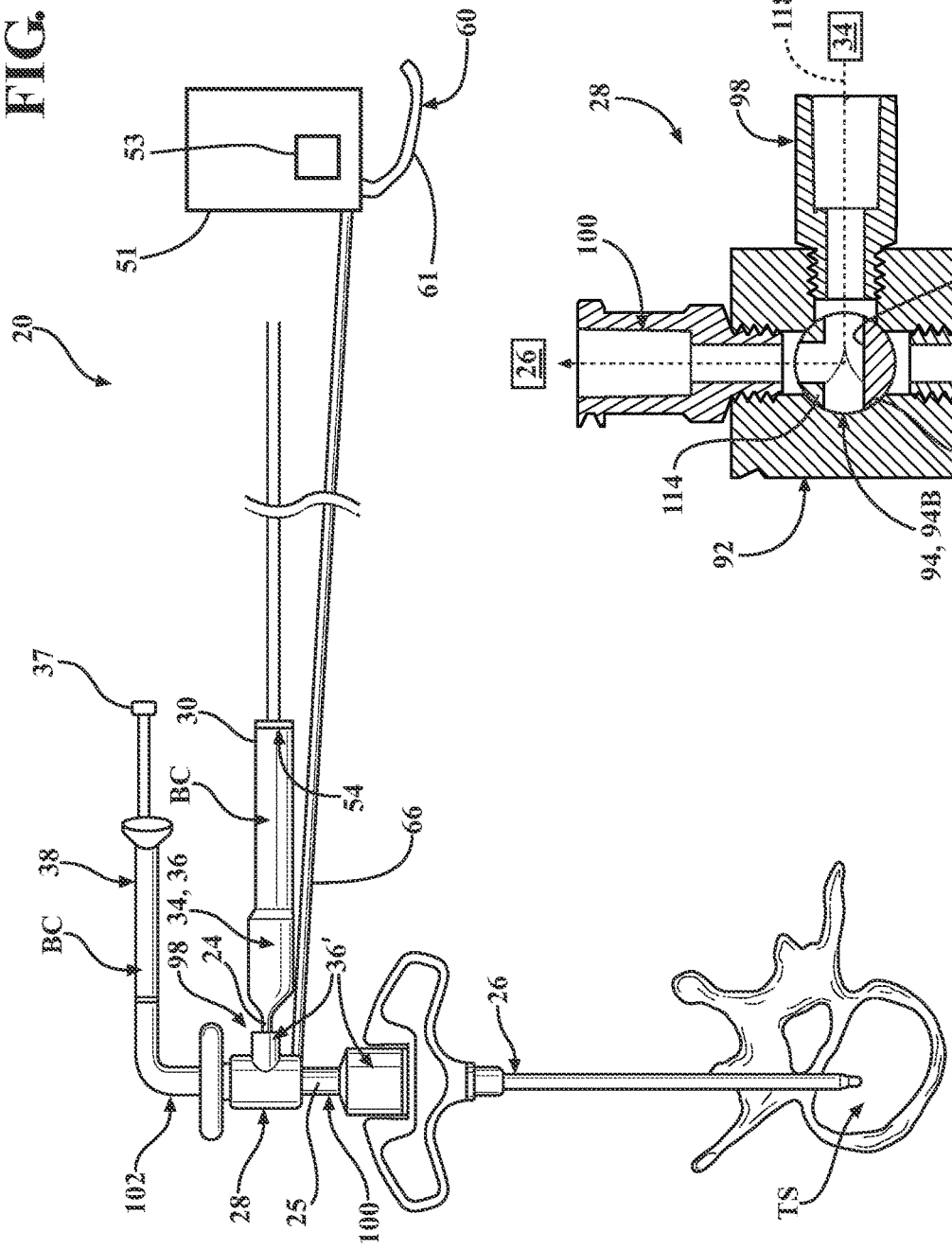

BONE CEMENT DELIVERY SYSTEMS INCLUDING A FLOW DIVERTER AND DROOL ACCUMULATOR

PRIORITY CLAIM

This is a continuation of copending U.S. application Ser. No. 16/487,615, filed on Aug. 21, 2019, which is a national stage entry of International Patent Application No. PCT/US2018/019211, filed on Feb. 22, 2018, which claims priority to and all the benefits of U.S. Provisional Application No. 62/462,043, filed on Feb. 22, 2017, the entire contents of each are hereby incorporated by reference.

TECHNICAL FIELD

The embodiments disclosed herein relate, generally, to bone cement delivery systems and, more specifically, to a flow diverter for use with bone cement delivery systems.

BACKGROUND

In many surgical procedures, particularly orthopedic procedures, it is common practice to inject bone cement into a bone or joint structure for improving the stabilization, strength, rigidity and movement of the bone/joint structure. Such surgical procedures commonly include arthroplasty, vertebroplasty, or kyphoplasty procedures.

In a typical surgical procedure where bone cement is injected, a cement source is fluidly coupled to a delivery device to deliver bone cement to the desired location. To provide the desired stability to the desired bone/joint structure, the bone cement typically requires a high pressure to be applied to allow the bone cement to flow from the cement device to the desired location. As such, once the desired amount of bone cement is delivered to the desired bone/joint structure, the high pressure remains in the system which forces additional undesired bone cement out of the delivery cannula.

Therefore, there remains a need for systems and methods which allow precise control of the delivery of bone cement.

SUMMARY

A bone cement delivery system is disclosed herein and includes a plunger movably disposed in a cement reservoir having an exit port. The plunger is configured to selectively displace bone cement from the cement reservoir through the exit port. The system also includes an extension tube coupled to the exit port of the cement reservoir. The extension tube has a length sufficient to enable an operator of the system to avoid radiation exposure. Additionally, the system includes a flow diverter comprising a diverter inlet, a first diverter outlet, and a second diverter outlet with the diverter inlet being coupled to and downstream of the extension tube. The system also includes a cannula coupler configured for connection to a delivery cannula for directing the bone cement to a target site. The cannula coupler has a cannula coupler inlet and being downstream of the flow diverter. Moreover, the system includes a drool accumulator defining a drool volume for receiving residual bone cement. The drool accumulator has a drool inlet and is downstream of the flow diverter. The first diverter outlet is coupled to the cannula coupler inlet and the second diverter outlet is coupled to the drool inlet. The flow diverter includes a valve arranged for selective movement between a first configuration where fluid communication is established between the cement reservoir and the drool volume; and where fluid communication is interrupted between the cement reservoir and the cannula coupler; and a second configuration where fluid communication is established between the cement reservoir and the cannula coupler; and where fluid communication is interrupted between the cement reservoir and the drool volume. Finally, the system includes a user input mechanism which includes a control surface operably configured to actuate movement of the valve between the configurations.

A method for delivery of bone cement to a target site is further provided. The method includes displacing the bone cement through an extension tube towards a flow diverter by applying pressure to a plunger, delivering the bone cement through the flow diverter to the target site, and collecting a volume of bone cement distal the extension tube in a drool accumulator such that no residual bone cement from the extension tube is delivered to the target site.

These systems and methods allow precise control over the amount of bone cement delivered to the target site regardless of the amount of pressure remaining in the system once the desired amount of bone cement is delivered. This configuration helps prevent patient injury due to an excess amount of bone cement being delivered to the target site.

BRIEF DESCRIPTION OF THE DRAWINGS

Advantages of the present invention will be readily appreciated as the same becomes better understood by reference to the following detailed description when considered in connection with the accompanying drawings wherein:

FIG. 1A is a cross-sectional view of a linkage of the bone cement delivery system according to the embodiment of FIG. 1.

FIG. 9 is an enlarged perspective view of the flow diverter of FIGS. 5 and 6.

FIG. 10 is an exploded perspective view of the flow diverter of FIG. 9.

FIG. 14 is another sectional view depicting the pushrod and valve of FIG. 12 with the valve shown in a second configuration.

FIG. 15 is another sectional view depicting the valve of FIG. 13 with the valve shown in a second configuration and defining a second flow path.

FIG. 16 is another sectional view depicting the valve shown in an additional configuration and defining a third flow path.

FIG. 16A is another section view depicting the valve shown in FIG. 16 in an additional configuration.

FIG. 17 is a right-side plan view of a bone cement delivery system comprising a delivery device, with a flow diverter according to one embodiment coupled to the delivery device.

DETAILED DESCRIPTION

With reference to the drawings, where like numerals are used to designate like structure throughout the several views, a bone cement delivery system is generally indicated at 20 in FIGS. 1-6. The bone cement delivery system 20 is configured to facilitate injection of a bone cement BC into a target site TS. Examples of target sites include medullary canals for total hip arthroplasty procedures, vertebral bodies for vertebroplasty or kyphoplasty procedures, and other target sites TS in which bone cement BC is used.

The bone cement BC is typically a uniformly mixed bone cement; however, it is also contemplated that the bone cement may be non-uniform or otherwise without departing from the spirit of the invention. Bone cement BC as used herein may be any type of bone cement as known by one of ordinary skill in the art including but not limited to materials (e.g., composites, polymers, and the like) that have a fluid or flowable state or phase and a hardened, solid or cured state or phase. Curable materials include, but are not limited to, injectable bone cements (such as polymethylmethacrylate (PMMA) bone curable material), which have a flowable state wherein they can be delivered (e.g., injected) by a cannula to a site and subsequently cure into hardened, cured material. Other materials such as calcium phosphates, bone in-growth materials, antibiotics, proteins, or combinations thereof, can be used in place of, or to augment bone cement (but do not affect an overriding characteristic of the resultant formulation having a flowable state and a hardened, solid, or cured state). Some materials may allow the body to reabsorb the curable material and/or improve the clinical outcome based on the type of filler implant material.

Figure 1:
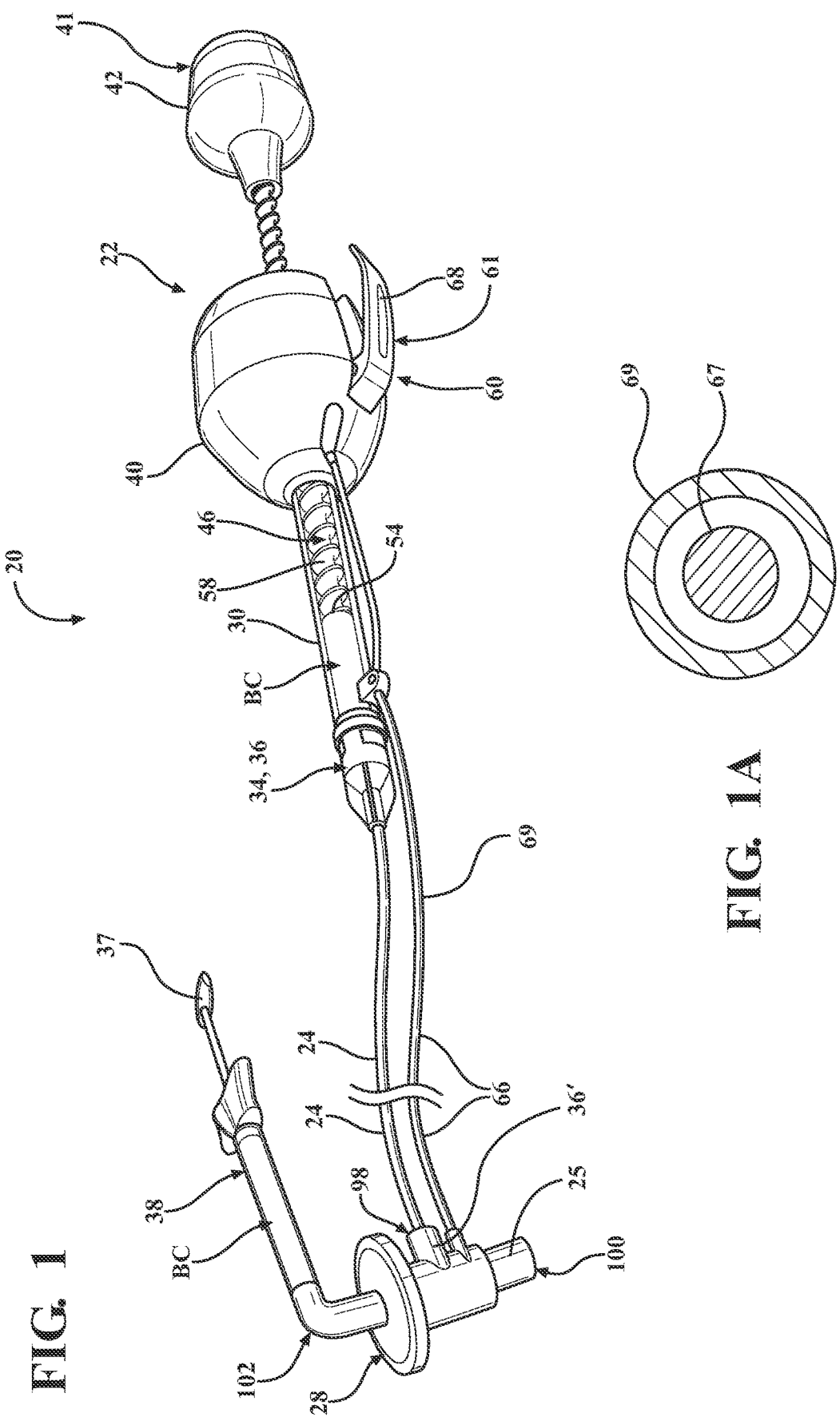
FIG. 1 is a broken perspective view of a bone cement delivery system comprising a delivery device coupled to a flow diverter according to one embodiment.
Figure 2:
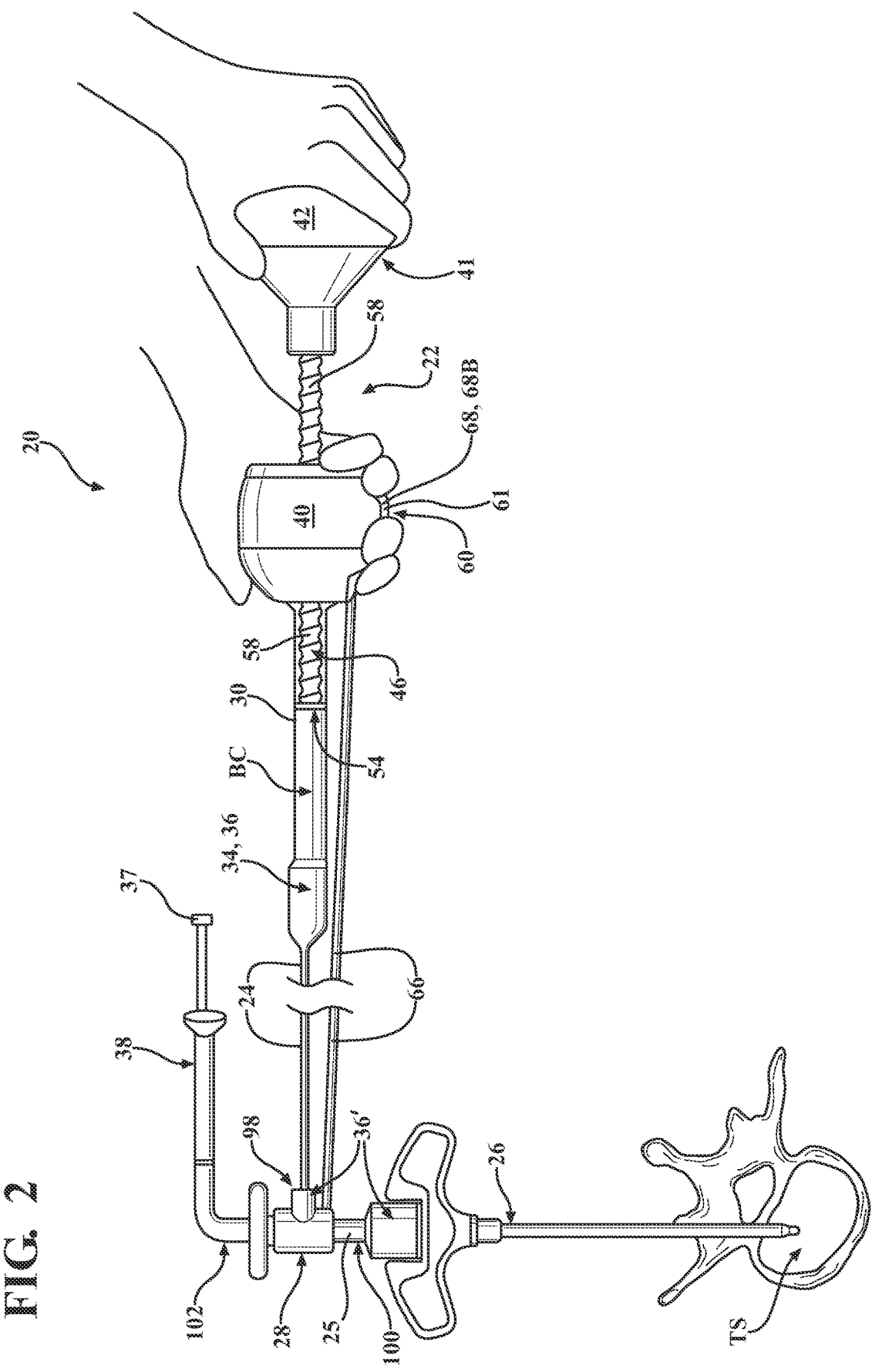
FIG. 2 is a broken right-side plan view of a bone cement delivery system comprising a delivery device supported by a user, with a flow diverter according to one embodiment coupled to the delivery device, the flow diverter shown coupled to a drool accumulator and to a delivery cannula.
Figure 3:
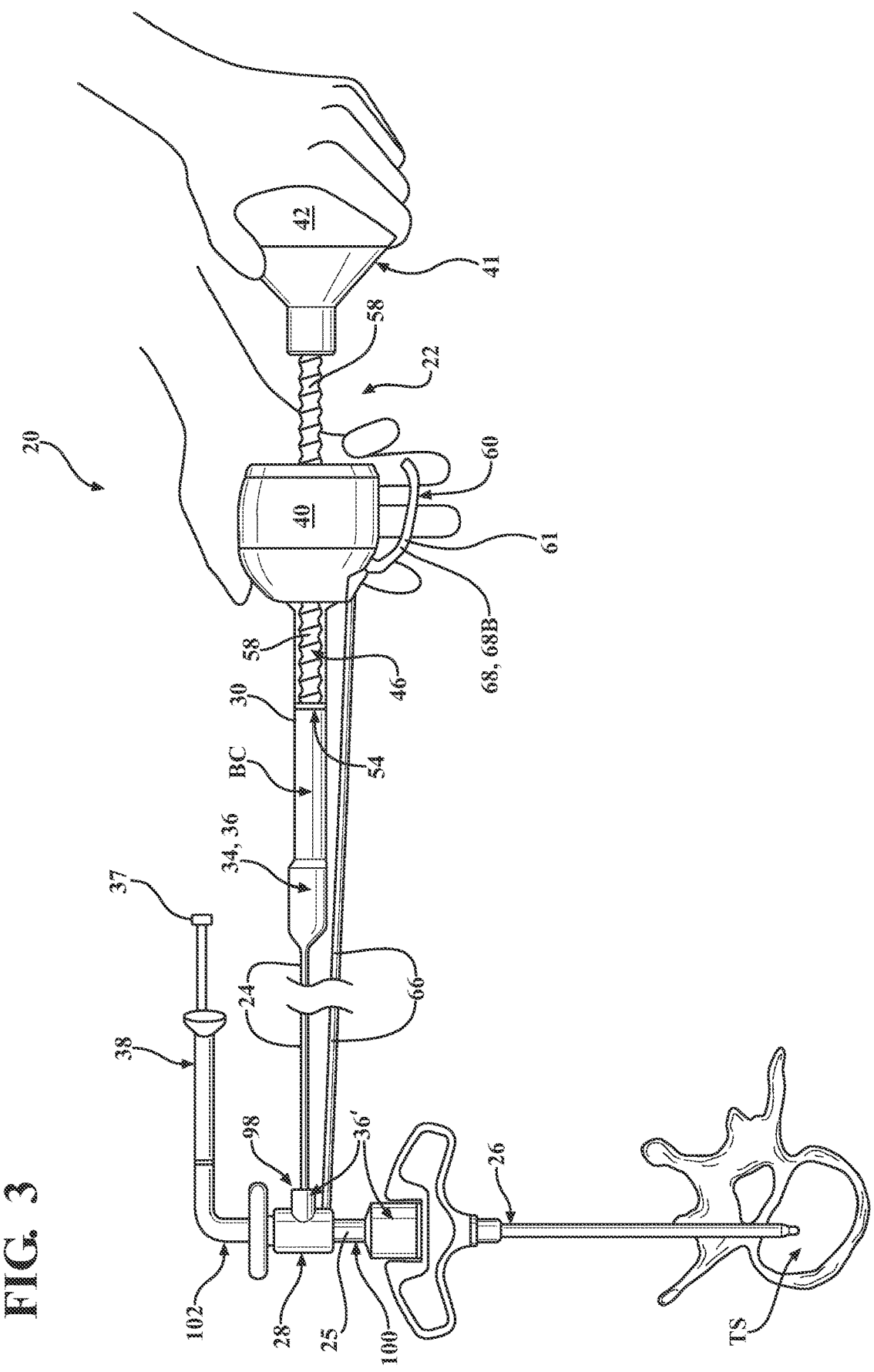
FIG. 3 is another broken right-side plan view of the bone cement delivery system of FIG. 2, shown with the user supporting the delivery device in another configuration.
Figure 4:
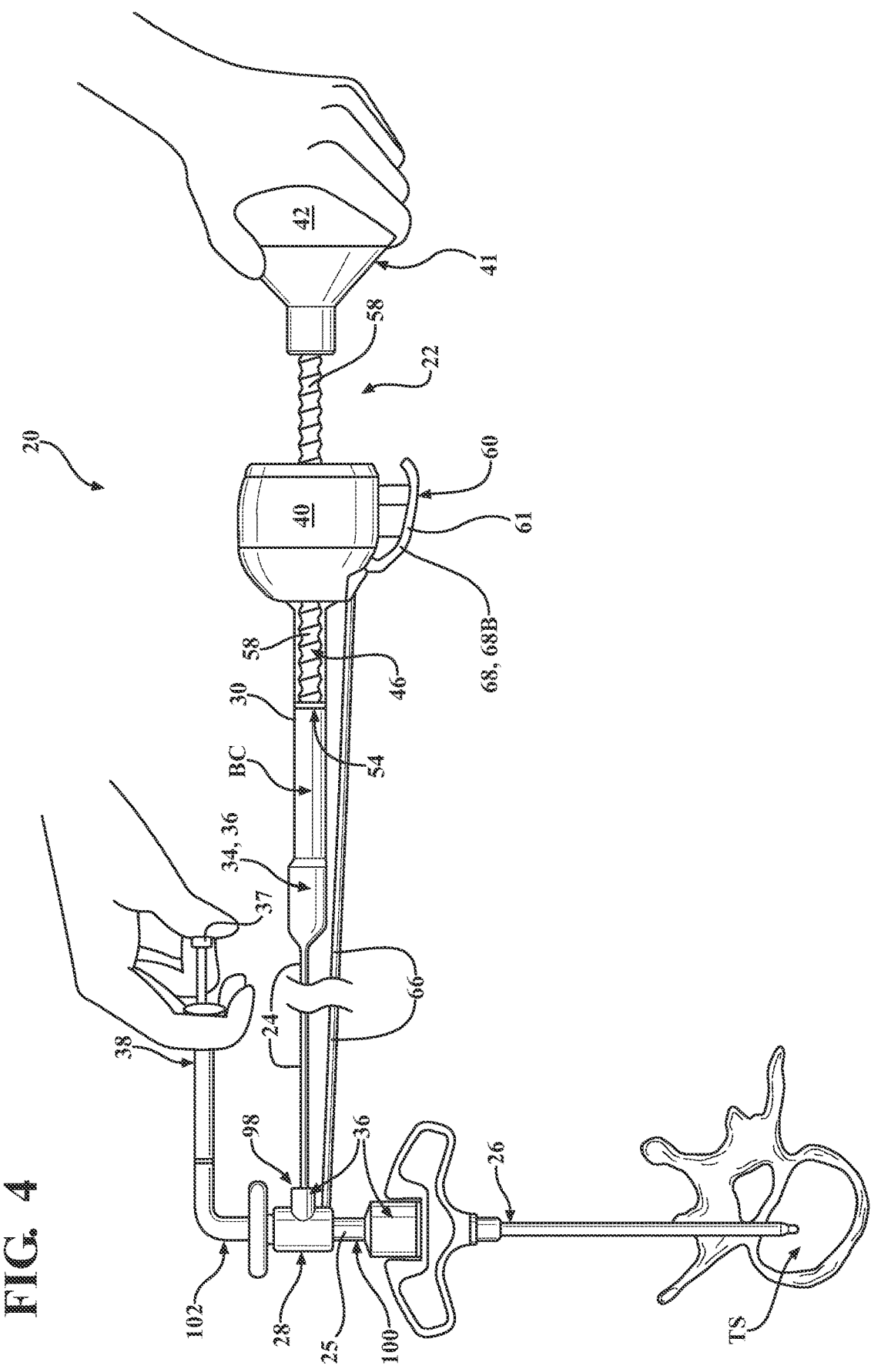
FIG. 4 is another broken right-side plan view of the bone cement delivery system of FIGS. 2-3, shown with the user supporting the delivery device in a third configuration.
Figure 5:
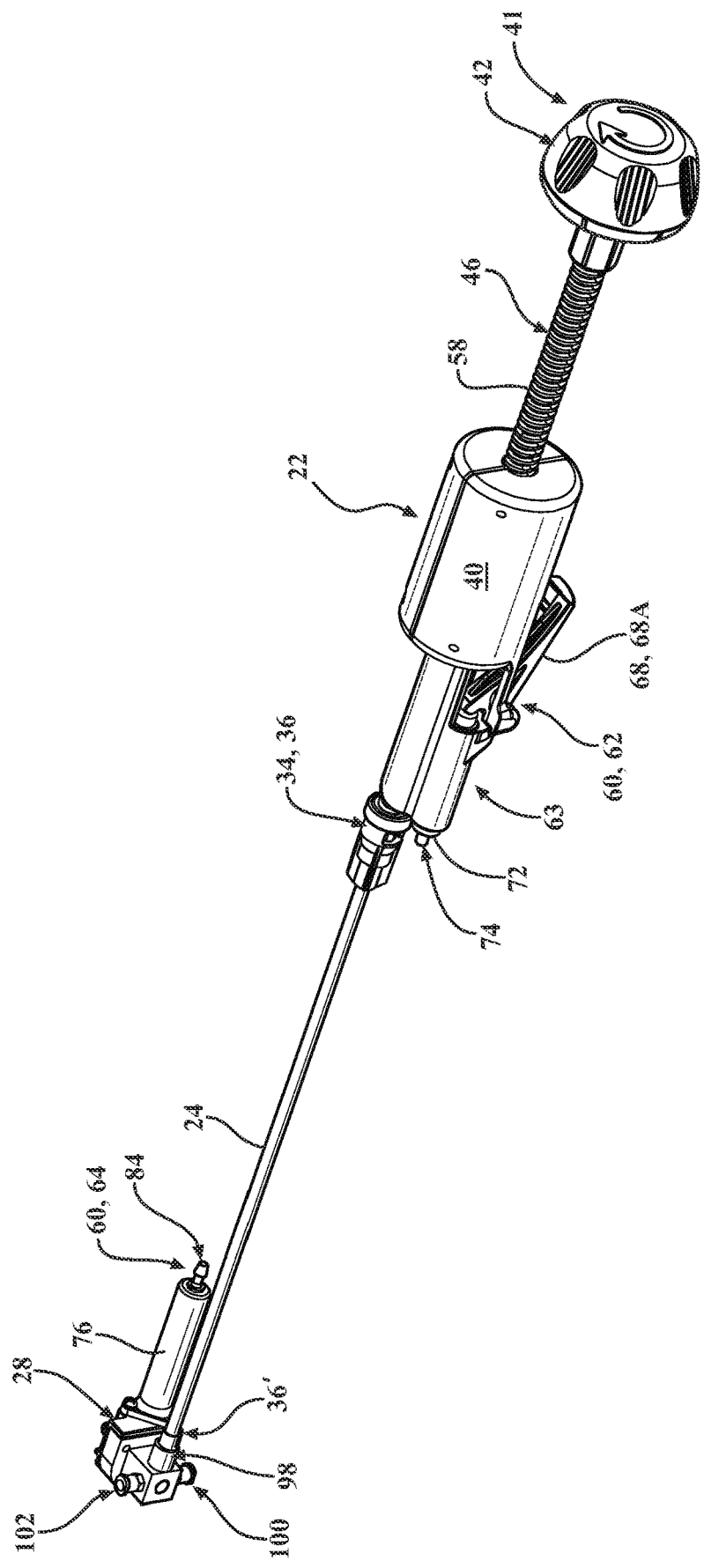
FIG. 5 is a perspective view of a bone cement delivery system comprising a delivery device and a flow diverter according to another embodiment.

As is best shown in FIGS. 1-4, the bone cement delivery system 20 generally comprises a delivery device 22, an extension tube 24, a cannula coupler 25 configured for connection with a delivery cannula 26, a drool accumulator 38, and a flow diverter 28 according to one aspect of the design. In certain configurations, the extension tube may be omitted, and the delivery device may be directly coupled to the flow diverter. The cannula coupler 25 is configured to be coupled directed to the delivery cannula 26 and arranged for on-axis or off-axis delivery of bone cement BC to the target site TS. For example, FIGS. 2-4 show the delivery cannula 26 defining a lumen having an outlet configured to direct the bone cement BC within a vertebral body defining the target site TS. In one exemplary embodiment, the delivery cannula 26 is configured for insertion into a bone site of interest in a patient. The delivery cannula 26 may also receive a cavity forming device to create a cavity at the target site TS. For example, the cavity forming device may be an expandable member directed through the lumen of the delivery cannula 26. For another example, the cavity forming device may include a stylet having a pre-curved distal section formed from shaped-memory material (e.g., Nitinol). The pre-curved distal section is straightened when directed through the lumen of the delivery cannula 26, thereafter returning to the curved shape after exiting the delivery cannula 26 at or near the target site. The physician may manipulate the stylet to displace material (e.g., cancellous bone) to form the cavity. Exemplary systems and methods of forming cavities at a target site are disclosed in commonly-owned U.S. Pat. Nos. 8,226,657; 8,771,278; 8,894,658; 9,095,393; 9,158,078; 9,526,551; and 9,839,443, each of which is hereby incorporated by reference in its entirety. Alternatively, delivery cannula 26 itself may comprise the cavity forming device. Once the cavity is created, the cavity forming device may be removed from the lumen of the delivery cannula 26 and the lumen may be used to deliver the bone cement BC to the target site TS. It is also contemplated that an additional delivery tube may be placed in the lumen of the delivery cannula 26 prior to delivery of the bone cement BC to the target site TS. Moreover, it is contemplated that the cavity may be created prior to the delivery cannula 26 being inserted in the target site TS. Additionally, it is also contemplated that no cavity is created prior to the delivery of the bone cement BC. The delivery cannula 26 may be comprised of surgical grade stainless steel, a plastic polymer, or another material as known by one of ordinary skill in the art.

As is described in greater detail below, the delivery device 22 comprises a cement reservoir 30 adapted to receive bone cement BC through an entry port 32 (see FIG. 6) or through other openings for subsequent dispersal out of an exit port 34. In one embodiment, the exit port 34 is adapted for releasable attachment to a proximal end of the extension tube 24 via a coupling arrangement, generally indicated at 36, such that bone cement BC flowing out of the exit port 34 of the reservoir 30 enters and flows along the extension tube 24. At a proximal end of the extension tube 24, another coupling arrangement 36' is employed to releasably attach the extension tube 24 to the flow diverter 28. The coupling arrangements 36, 36' may assume any suitable configuration that allows high-pressure fluid joints to be formed.

The flow diverter 28 allows a user to selectively direct bone cement BC to either the cannula coupler 25 coupled with the delivery cannula 26, such that the bone cement BC flows through the delivery cannula 26, or to a drool volume of a drool accumulator 38. As is described in greater detail below, in one configuration, the flow diverter 28 allows the user to control the flow of bone cement BC from the cement reservoir 30 towards either the delivery cannula 26 to direct bone cement BC to the target site TS, or towards the drool accumulator 38 where residual bone cement is received. As used herein, the term residual bone cement is bone cement which is subject to residual elevated pressure following dispensing of the bone cement BC such that the bone cement BC will continue to flow after the delivery device 22 has ceased to be activated. In other words, the movement of the plunger 46 to displace the bone cement BC out of the exit port of the reservoir 30 causes a pressure build up in the volume of bone cement which causes flow of the bone cement BC. Once the user determines the desired amount of bone cement BC has been moved into the target site TS, the user will stop actuating the cement delivery input mechanism 41. However, the bone cement BC that remains in the cement reservoir 30, the extension tube 24, and the delivery cannula 26 will still have an elevated pressure such that the bone cement BC will continue to flow towards the target site TS. Residual bone cement therefore, is defined as any cement remaining in the bone cement BC delivery system when the plunger 46 is stationary following previous actuation of the delivery device 22.

As noted above, the representative aspect of the delivery device 22 depicted herein is configured to receive pre-mixed bone cement BC into the cement reservoir 30 and to subsequently allow the user to direct bone cement BC towards the target site TS via the delivery cannula 26. However, those having ordinary skill in the art will appreciate from the subsequent description of the flow diverter 28 below that different types of delivery devices 22 are contemplated herein. By way of non-limiting example, the delivery device 22 could also be adapted to mix bone cement BC, such as within the reservoir 30, prior to or during injection towards the target site TS. Exemplary systems and methods of mixing bone cement within the reservoir 30 are disclosed in commonly-owned U.S. Pat. Nos. 6,547,432; 6,736,537; 7,134,782; 7,306,361; 7,320,540, each of which is hereby incorporated by reference in its entirety. In one exemplary embodiment, the cement reservoir 30 is a conventional syringe comprised of a plastic polymer, glass, or metal. However, it is also contemplated that the cement reservoir 30 may be any container as known by one of ordinary skill in the art configured to hold a volume of bone cement BC. In one embodiment, the cement reservoir 30 and the corresponding bone cement are as described in WO Pub. No. 2008/045329A2 which is hereby incorporated by reference herein.

Figure 6:
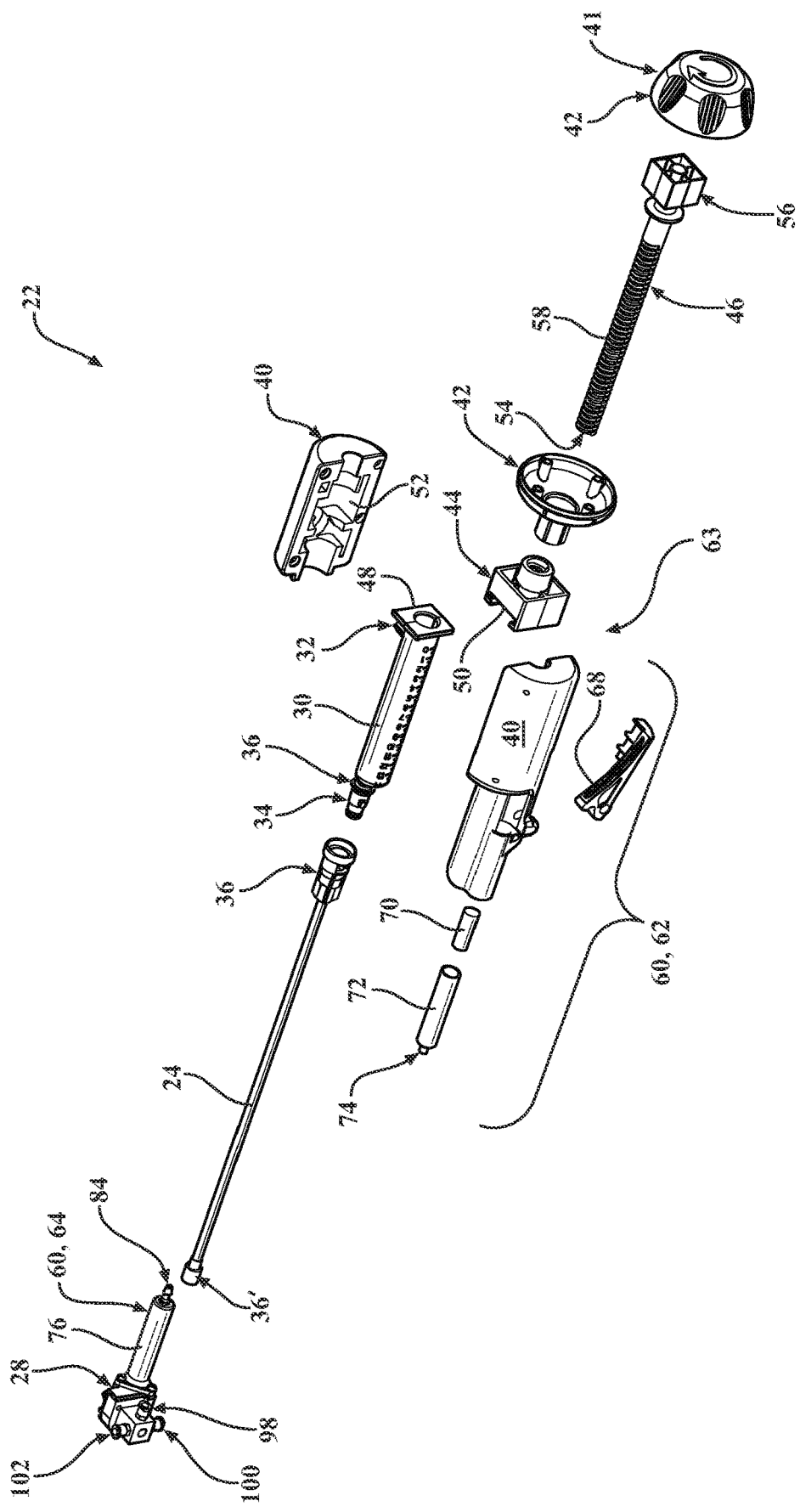
FIG. 6 is an exploded perspective view of the bone cement delivery system of FIG. 5.
Figure 7:
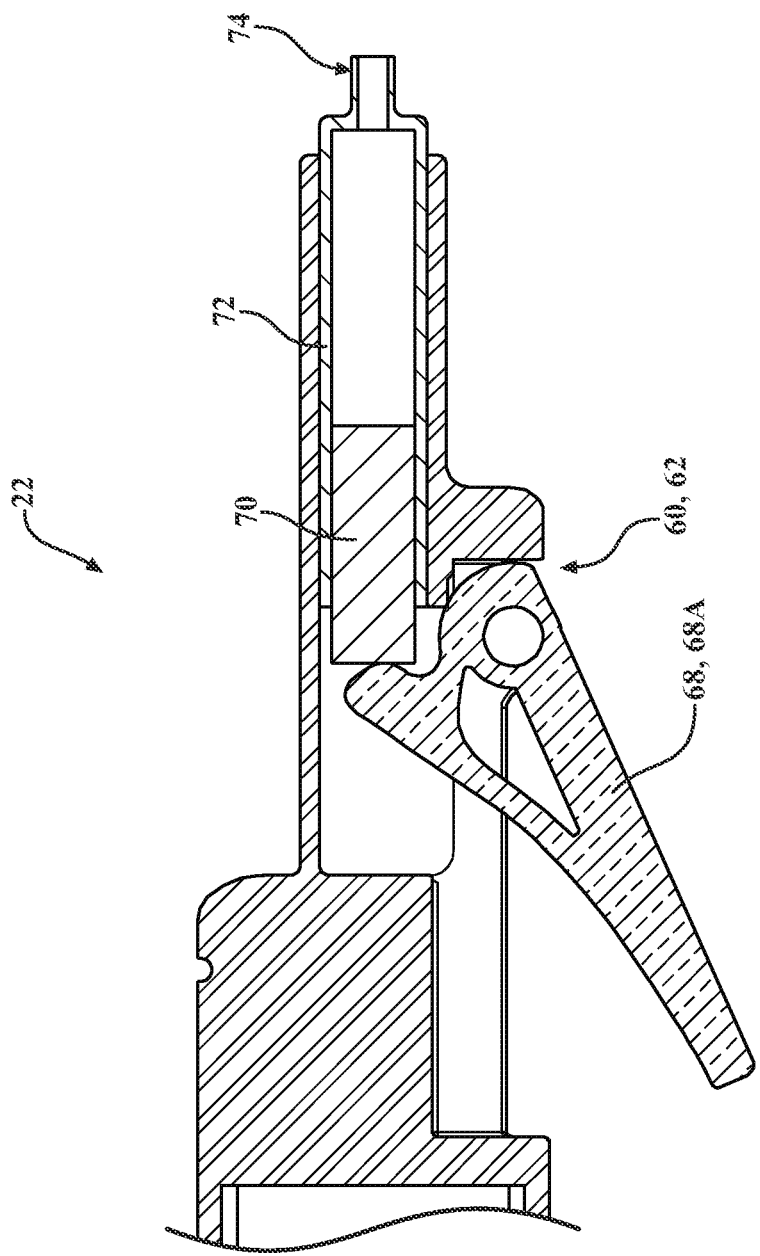
FIG. 7 is a broken sectional view of a portion of the bone cement delivery system of FIGS. 5-6, depicting a user input mechanism in a released configuration.
Figure 8:
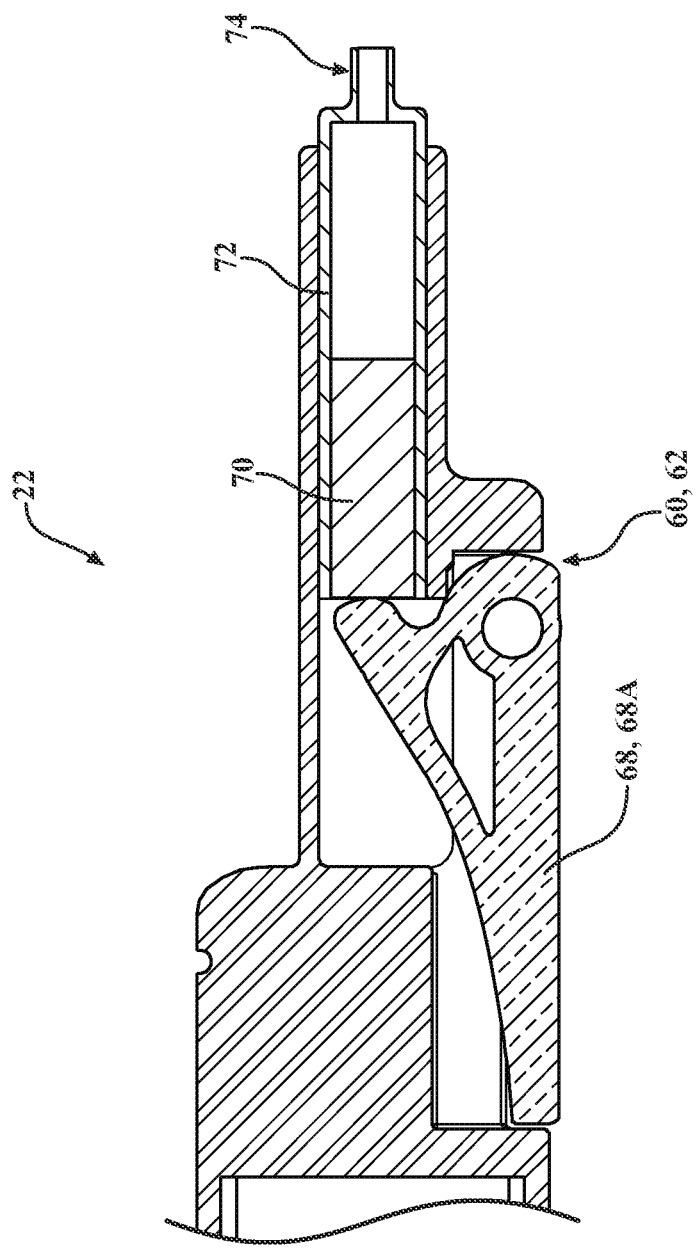
FIG. 8 is another broken sectional view of the portion of the bone cement delivery system of FIG. 7, shown with the user input mechanism in an engaged configuration.
Figure 11:
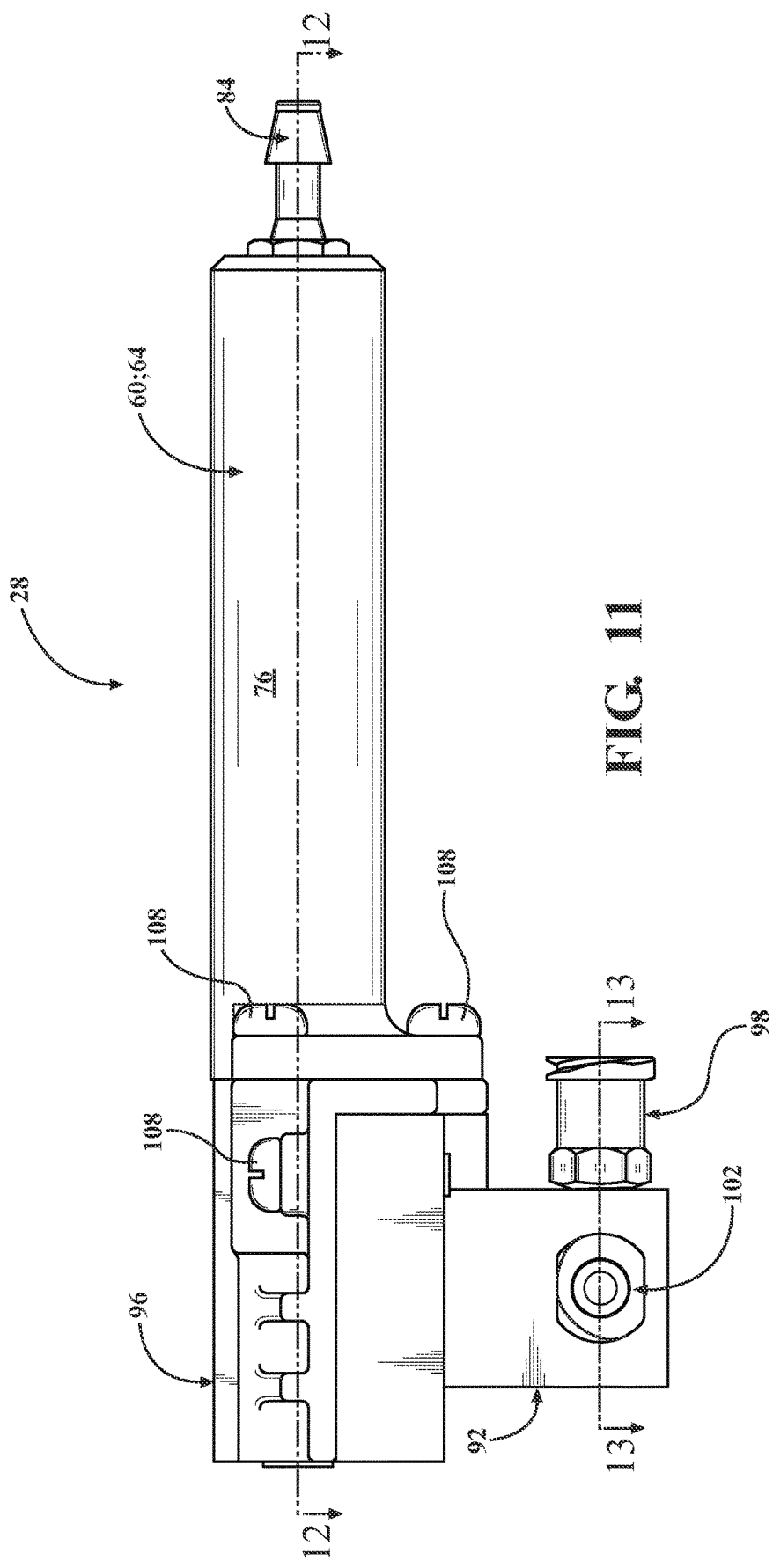
FIG. 11 is a top-side plan view of the flow diverter of FIGS. 9-10.
Figure 12:
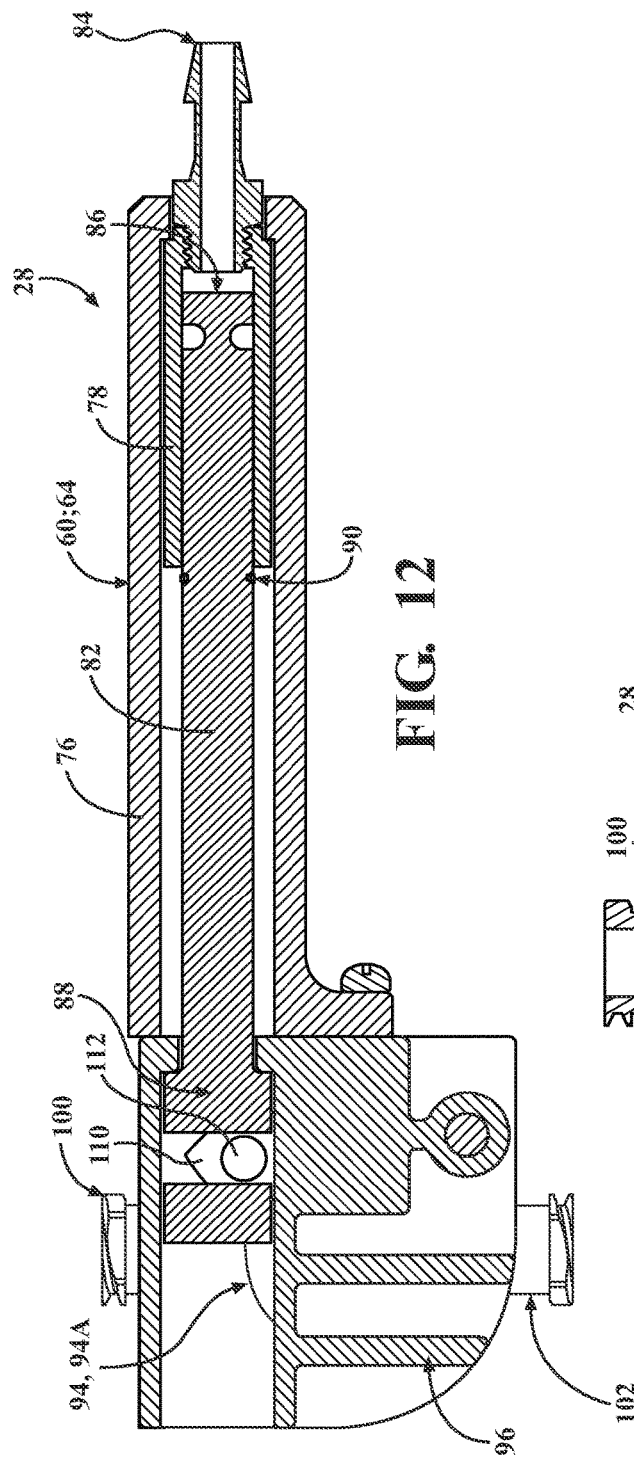
FIG. 12 is a sectional view taken along line 12-12 of FIG. 11, depicting a pushrod and a valve with the valve shown in a first configuration.

With reference to FIGS. 1-6, in the illustrated design, the delivery device 22 further comprises a handle 40, a cement delivery input mechanism 41, a nut 44, and a plunger 46. Typically, the entire delivery device 22 including but not limited to the handle 40, the cement delivery input mechanism 41, the nut 44, and the plunger 46 are arranged upstream of the extension tube 24. However, other configurations have also been contemplated. As illustrated in FIGS. 1-6, in one embodiment, the cement delivery input mechanism 41 is configured as a knob 42 or other rotational actuator, configured to be rotated to actuate movement of the plunger to displace the bone cement BC from the cement reservoir 30, however, it is also contemplated that the cement delivery input mechanism 41 may be another mechanism configured to actuate movement of the plunger to displace the bone cement BC from the cement reservoir 30. In this embodiment, as is best shown in FIG. 6, both the handle 40 and the knob 42 are realized as two-piece components which are coupled to one another so to facilitate assembly of the delivery device 22. However, other configurations are contemplated including any conventional handle configured for ease of holding the bone cement delivery system 20 by a user. The cement delivery input mechanism 41 could alternatively take the form of a lever or other actuator configured to move the plunger distally upon engagement by the user.

In the embodiment illustrated in FIGS. 1-6, the handle 40 is generally cylindrical and supports the cement reservoir 30 via a flange 48 formed at a proximal end of the reservoir 30 which is received in a correspondingly-shaped flange receptacle 50 formed in the nut 44. While the handle 40 is depicted throughout the drawings as having a generally tapered-cylindrical profile, those having ordinary skill in the art will appreciate that the handle 40 could have any suitable profile, shape, or configuration. By way of non-limiting example, the handle 40 and/or other components of the delivery device 22 could be configured to provide a "pistol grip" configuration.

Referring still to the embodiment illustrated in FIGS. 1-6, the nut 44 of the delivery device 22 has a generally rectangular configuration and is supported in a correspondingly-shaped pocket 52 formed in the handle 40. The plunger 46 comprises a distal working end 54, a proximal end 56, and a shaft 58 arranged between the working end 54 and the proximal end 56. The working end 54 of the plunger 46 is at least partially disposed within the cement reservoir 30 and is adapted for engagement with bone cement BC within the cement reservoir 30. The proximal end 56 of the plunger 46 may be received by and rotate concurrently with the knob 42, and the shaft 58 may be disposed in threaded engagement with the nut 44 such that rotation of the knob 42 relative to the handle 40 affects movement of the working end 54 along the reservoir 30. Thus, rotation of the knob 42 causes the working end 54 of the plunger 46 to move within the reservoir 30 so as to control the flow of bone cement BC stored within the reservoir 30 out of and/or back into the exit port 34. Put differently, rotation of the knob 42 in one direction advances bone cement BC out of the reservoir 30 via the exit port 34, and rotation of the knob 42 in an opposite direction retracts bone cement BC back into the reservoir 30 via the exit port 34. In certain embodiments, an automatic or user-activated interrupt mechanism may be provided to allow for or otherwise facilitate retraction of bone cement BC without necessitating rotation of the knob 42.

As described above, the delivery device 22 can be configured in a number of different ways, and can employ any suitable number of components, arranged and/or configured in any suitable way sufficient to facilitate injection of bone cement BC towards the target site TS. In another embodiment, illustrated in FIG. 17, the cement delivery input mechanism 41 comprises a control surface coupled to a hydraulic system 51 having a hydraulic pump 53 configured to displace a plunger to cause displacement of bone cement BC out of the cement reservoir 30 towards the target site TS. The hydraulic system 51 and the hydraulic pump 53 may be as described in U.S. Pat. No. 8,361,078, which is hereby incorporated by reference. However, it is also contemplated that the hydraulic system 51 and the hydraulic pump 53 may be of another configuration. The control surface may be coupled to a valve that allows selective transmission of hydraulic fluid through various reservoirs of the hydraulic system. In other words, the hydraulic system may be configured to move the plunger distally to advance bone cement BC out of the reservoir 30 via the exit port 34. In this embodiment, the distance to avoid radiation exposure is provided by the hydraulic system 51 itself. In other words, actuation of the hydraulic system 51 may be controlled remotely from the surgical site such that the physician may not be required to manually support the delivery device 22 as the bone cement BC is advanced out of the reservoir 30. With the physician positioned away from the delivery device 22, potential radiation exposure is lessened such that no extension tube may be necessary. In such an embodiment, the cement reservoir 30 may be disposed adjacent or directly coupled to the flow diverter 28 (e.g., with no intervening extension tube).

Referring again to the embodiments illustrated in FIGS. 1-4, the drool accumulator 38 is coupled to and disposed downstream of the flow diverter 28 and defines a drool volume for receiving the residual bone cement. As such, the drool accumulator 38 may be any container configured to define the drool volume. In certain embodiments, such as the embodiment illustrated in FIG. 1, the drool accumulator 38 is realized as a conventional container such as a transparent syringe, having visual indicators, which may be removably attached (or, permanently coupled) to the second diverter outlet 102 of the flow diverter 28. It will be appreciated that this configuration affords the user with a visible indicia corresponding to the volume of residual bone cement collected in the drool accumulator 38 during use. In other embodiments, the drool accumulator 38 could be realized with an expandable or flexible material, a collection tray or container, and the like. However, those having ordinary skill in the art will appreciate that the flow diverter 28 and/or the drool accumulator 38 could be configured in a number of different ways, and from a number of different components. By way of non-limiting example, while residual bone cement is stored in the drool accumulator 38, it is conceivable that the flow diverter 28 could be configured to direct residual bone cement back towards the reservoir 30. Further, as best illustrated in FIG. 4, the flow diverter 28 could be configured such that the drool accumulator 38 includes an actuator 37 configured to be actuated by a user to displace bone cement BC out of the drool accumulator 38 and back towards the flow diverter 28, and ultimately towards the cannula coupler 25, and through the delivery cannula 26. This configuration could be used to effect more precise, localized re-direction of bone cement BC towards the target site TS.

Moreover, while the drool accumulator 38 is disposed adjacent to the target site TS and downstream of the extension tube 24 in the illustrated example of FIGS. 1-4, it will be appreciated that the drool accumulator 38 could be positioned in any suitable location. By way of non-limiting example, the drool accumulator 38 could be arranged adjacent to delivery device 22, i.e., proximal the extension tube 24.

As used herein, the drool volume is defined as a volume of matter which is collected in the drool accumulator 38. In some cases, the drool volume will include residual bone cement while in other cases the drool volume will only include pressure from the system. More specifically, as described in more detail below, applying pressure to the plunger 46 to displace the bone cement BC from the cement reservoir 30 inherently increases the pressure of all of the bone cement BC in the system. The increased pressure is exacerbated by the flexibility and/or elastic expansion and contraction of certain components, such as the extension tube 24, during use. The increased pressure in the system remains even after the pressure to the plunger 46 is ceased. This may cause undesirable movement of residual bone cement into the target site TS after the desired amount of bone cement BC has been delivered to the target site TS. As such, the flow diverter 28 is configured to direct the residual bone cement to the drool accumulator 38 to prevent the residual bone cement from being delivered to the target site TS. Therefore, depending on the pressure of the residual bone cement in the system when the flow diverter 28 is configured to direct the residual bone cement to the drool accumulator 38, the drool volume which is accumulated in the drool accumulator 38 may be a mixture of bone cement BC and pressurized gas from the system or may be pressurized gas alone such that the bone cement BC does not reach the drool accumulator 38.

Advantageously, in certain embodiments as illustrated in FIGS. 2-4, the flow diverter 28 is located in close proximity to the delivery cannula 26, spaced from exit port 34 of the delivery device 22 via the extension tube 24 such that the flow diverter 28 is disposed downstream of the extension tube 24. This arrangement may provide more precise control over the residual bone cement such that any residual bone cement in the extension tube 24 can be diverted by the flow diverter 28 towards the drool accumulator 38, if desired.

The extension tube 24 may be flexible so as to allow the user to position or otherwise manipulate the delivery device 22 relative to the delivery cannula 26 at the target site TS. Here, the extension tube 24 is configured with sufficient length to position the delivery device 22 away from the target site TS, such as a length sufficient to distance the user from radiation emitted in connection with fluoroscopy. In some embodiments the length of the extension tube 24 is approximately 200-400 centimeters, and in one embodiment approximately 300 centimeters, although any length of extension tube 24 may be used. In other embodiments, such as the embodiment where the delivery device 22 includes the hydraulic system, the length sufficient to allow the user to remain at a safe distance from radiation is provided by the hydraulic system itself such that no extension tube is needed. This length may be provided by a tube coupling the hydraulic pump 53 with the plunger 46 such that the tube delivers pressurized fluid from the hydraulic pump 53 to the cement reservoir 30. When used, the extension tube 24 may be comprised of a material which allows sufficient strength to control the position of the delivery cannula 26 into the target site TS throughout the length of the extension tube 24 and configured to withstand pressures of up to 4000 psi, as a typical operating pressure in the extension tube 24 may be between 500-2000 psi. The extension tube 24 is also of sufficient strength to allow the pressurized bone cement BC to move from the cement reservoir 30 to the flow diverter 28. In one exemplary embodiment, the extension tube 24 comprises plastic. However, it is also contemplated that the extension tube 24 may be comprised of a metal, glass, a composite material, or the like. The extension tube 24 may be reinforced with a metal braid or liner.

As best illustrated in FIGS. 1-4, in order to facilitate operation of the flow diverter 28 a user input mechanism 60 comprising a control surface, generally indicated at 61, is provided. The user input mechanism is configured to allow the user to actuate the flow diverter 28. In one exemplary embodiment, illustrated in FIGS. 1-4, the control surface is a trigger 68 but it is also contemplated that the control surface may be any other surface configured to be actuated by the user. Typically, the user input mechanism is disposed upstream of the flow diverter 28 via the extension tube 24, as illustrated in FIGS. 1-4. However, any configuration may be employed. In one embodiment, illustrated in FIGS. 1 and 1A, the user input mechanism 60 could employ a control surface configured for engagement by a user which actuates a linkage 66 realized as a wire 67 slidably movable within a conduit 69. More specifically, in the embodiment illustrated in FIG. 1, the user input mechanism 60 is coupled with the wire 67 which is coupled on an opposite end with the flow diverter 28. When the user input mechanism 60 is actuated, the wire 67 will slide within the conduit 69 to move a valve 92 of the flow diverter 28 between configurations. In one embodiment, the conduit housing is configured to protect the wire from debris or other interference from moving the valve 92 of the flow diverter 28 between configurations. In one exemplary embodiment, the conduit is comprised of a plastic polymer, however is it also contemplated that the conduit may be comprised of a rubber, metal, a composite material, or the like.

In another embodiment, illustrated in FIGS. 2-10, a user input actuation mechanism 63 comprises a master 62 coupled to the delivery device 22, a slave 64 coupled to the flow diverter 28, and a linkage 66 interposed in force-translating relationship between the master 62 and the slave 64. As is described in greater detail below, the master 62 is adapted for actuation by the user to effect corresponding actuation of the slave 64 which, in turn, controls the flow diverter 28. In the representative embodiment illustrated herein, the user input actuation mechanism 63 is realized as a hydraulic system whereby hydraulic fluid flows along the linkage 66 (for example, a tube, hose, line, and the like) between the master 62 and the slave 64. However, those having ordinary skill in the art will appreciate that the user input actuation mechanism 63 could have any suitable configuration sufficient to facilitate operation of the flow diverter 28 spaced downstream from the delivery device 22 via the extension tube 24. Thus, the user input actuation mechanism 63 could employ one or more hydraulic, pneumatic, electric, or mechanical components to effect control of the flow diverter 28.

In the embodiment illustrated in FIGS. 2-10, the linkage between the flow diverter 28 and the user input actuation mechanism 63 is a hydraulic linkage. More specifically, in the embodiment illustrated in FIGS. 2-10, the master 62 of the user input actuation mechanism 63 comprises the user input mechanism 60, a master piston 70, a master cylinder 72, and a linkage outlet 74. In one embodiment, the user input mechanism 60 is a trigger 68. The trigger 68 is coupled to the handle 40, transmits force to the master piston 70, and is movable between a released configuration 68A (see FIG. 7) and an engaged configuration 68B (see FIG. 8). It will be appreciated that the location of the user input actuation mechanism 63 is not particularly limited and, thus, may be coupled to the delivery device 22 in any suitable way or may be formed as a separate component to be handled independently of the delivery device 22 for certain embodiments, such as adjacent the flow diverter.

In one exemplary embodiment, when the trigger 68 is in the released configuration, fluid communication is established between the cement reservoir 30 and the drool volume of the drool accumulator 38. Therefore, in order to deliver bone cement BC to the target site TS, the user must move the trigger 68 to the engaged configuration in order to establish fluid communication between the cement reservoir 30 and the cannula coupler 25. However, it is also contemplated that the engaged configuration of the trigger 68 may correspond with interrupting fluid communication between the cement reservoir 30 and the cannula coupler 25 while the released configuration corresponds with establishing fluid communication between the cement reservoir 30 and the cannula coupler 25.

Referring still to the embodiment illustrated in FIGS. 2-10, the linkage outlet 74 is disposed in fluid communication with the master cylinder 72 and is adapted to hydraulically couple to the slave 64 via the linkage 66. The master piston 70 is supported for movement within the master cylinder 72 in response to movement of the trigger 68, and is adapted to displace hydraulic fluid out of and back into the linkage outlet 74 to effect corresponding movement of the slave 64. To this end, and as is depicted in FIGS. 9, 10, 12, and 14, the slave 64 of the user input actuation mechanism 63 comprises a slave cylinder 76, a sleeve 78, a spring 80 (omitted from FIGS. 12 and 14), a pushrod 82, and a linkage inlet 84. The sleeve 78 is supported within the slave cylinder 76 and is coupled in fluid communication with the linkage inlet 84 which, in turn, is adapted to hydraulically couple to the master 62 via the linkage 66. The pushrod 82 extends between a proximal cylinder end 86 and a distal selector end 88, and supports a snap ring 90 between the cylinder end 86 and the selector end 88, which cooperates with the spring 80 to bias the pushrod 82 in certain embodiments. The cylinder end 86 is supported for movement within the sleeve 78 in response to the flow of hydraulic fluid into and out of the linkage inlet 84 via the hydraulic communication with the linkage outlet 74 of the master 62 via the linkage 66, as noted above.

Figure 13:
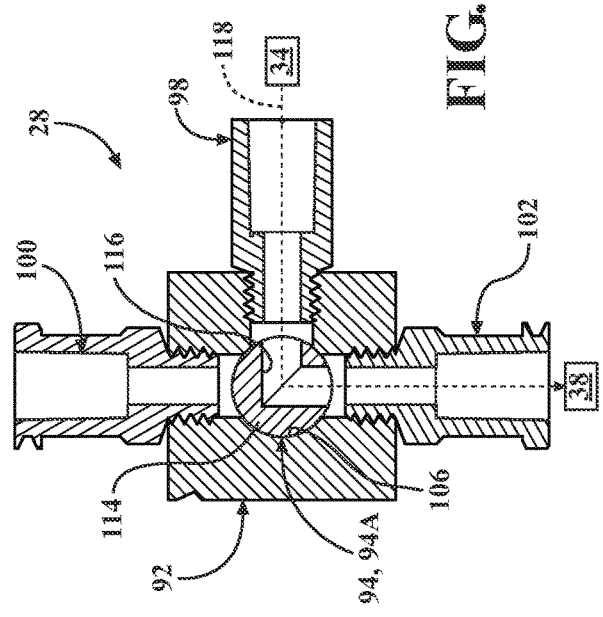
FIG. 13 is a sectional view taken along line 13-13 of FIG. 11, depicting a valve shown in the first configuration and defining a first flow path.

Referring now to FIGS. 13-15, the flow diverter 28 comprises the valve 92 arranged for selective movement between a first configuration and a second configuration. The valve 92 defines diverter inlet 98, a first diverter outlet 100, and a second diverter outlet 102, each of which is provided with a coupling arrangement 36 to facilitate attachment to the extension tube 24, the cannula coupler 25, and the drool accumulator 38, respectively. As such, a first flow path is defined between the cement reservoir 30 and the cannula coupler 25 when the valve 92 is in the second configuration (see FIG. 13). Additionally, a second flow path is defined between the cement reservoir 30 and the drool accumulator 38 when the valve 92 is in the first configuration (see FIG. 15). In other words, in the first configuration of the valve 92, fluid communication is established between the cement reservoir 30 and the drool volume. Additionally, in the first configuration fluid communication is interrupted between the cement reservoir 30 and the cannula coupler 25. Therefore, in the first configuration, the bone cement BC flows from the exit port of the cement reservoir 30 to the drool accumulator 38. In the second configuration of the valve 92, fluid communication is established between the cement reservoir 30 and the cannula coupler 25. Additionally, in the second configuration fluid communication is interrupted between the cement reservoir 30 and the drool volume. Therefore, in the second configuration, the bone cement BC flows from the exit port of the cement reservoir 30 to the cannula coupler 25 where the bone cement BC can then be delivered to the target site TS.

In a surgical procedure, an undesirable amount of bone cement BC may be received within the drool accumulator. To limit waste and/or to minimize the amount of bone cement BC required for the procedure, it may be desirable to direct the bone cement BC received within the drool accumulator 38 towards the target site TS. To that end, in another embodiment, illustrated in FIG. 16, in the first configuration fluid communication is established between the drool volume and the cannula coupler 25. Additionally, in the first configuration, fluid communication is interrupted between the cement reservoir 30 and the cannula coupler 25. Moreover, in the embodiment illustrated in FIG. 16A, in the second configuration of the valve 92, fluid communication is established between the cement reservoir 30 and the cannula coupler 25. Additionally, in the second configuration fluid communication is interrupted between the cement reservoir 30 and the drool volume and between the cement reservoir 30 and the cannula coupler 25. Therefore, in the first configuration, the residual bone cement BC between the valve 92 and the target site TS will move to the drool accumulator 38, and bone cement BC accumulated in the drool accumulator 38 can be displaced back through the flow diverter and into the cannula coupler 25 for delivery to the target site TS. Additionally, as illustrated in FIGS. 1-4, the drool accumulator 38 may include an additional plunger 37 activated by a user or other mechanism to displace the bone cement BC out of the drool accumulator 38 towards the target site TS. This configuration of having a flow path between the drool accumulator 38 and the cannula coupler 25 allows bone cement BC from the drool accumulator 38 to be delivered to the target site TS which may improve control of delivery, as represented schematically in FIG. 16. It is contemplated that this configuration may be included in the valve 92 as described herein as a third configuration. Additionally, it is contemplated that this configuration may be included in a second valve present in the system. The second valve may correspond to the first valve 92 such that movement of the first valve 92 corresponds with movement of the second valve, or the second valve may be a completely independent valve. In other words, the second valve may move dependently with the first valve 92 such that when the trigger 68 or other user input mechanism 60 is engaged, both the first valve 92 and the second valve move to another configuration. Moreover, it is contemplated that the bone cement delivery system may include a second user input mechanism configured to move only the second valve between configurations, when desired by the user.

Referring now to FIGS. 9-15, in one exemplary embodiment, described in more detail below, the valve 92 is a rotor valve such that the movement between the first configuration and the second configuration is rotational movement. However, it is also contemplated that the valve 92 may be any type of valve including but not limited to a ball valve, a pinch valve, a butterfly valve, a globe valve or the like. Additionally, the movement of the valve 92 between the first configuration and the second configuration may be any type of movement including but not limited to linear, translational, reciprocal, and/or oscillating motion. It is also contemplated that the flow paths defined in the first configuration and the second configuration may be defined using different valves such that multiple valves are present and working cooperatively within the system.

In one exemplary embodiment, illustrated in FIGS. 9-15, the flow diverter 28 comprises the valve 92, and a retainer 96. The valve 92 defines the diverter inlet 98, the first diverter outlet 100, the second diverter outlet 102, each of which is provided with a coupling arrangement 36 to facilitate attachment to the extension tube 24, the delivery cannula 26, and the drool accumulator 38, respectively. As is best shown in FIG. 10, a chamber 104 and a bore 106 are defined in the valve 92 so as to accommodate a rotor portion 94 of the valve 92. One or more fasteners 108 are employed to secure the slave 64 and the retainer 96 to the valve 92. The retainer 96 limits movement of the pushrod 82 and the rotor portion 94 with respect to the valve 92 during use.

As is best shown in FIG. 10, the rotor portion 94 comprises a cam head 110, a selector pin 112, and a shaft 114. The shaft 114 is rotatably supported within the bore 106 defined in the valve 92, and has a channel 116 defined adjacent to the diverter inlet 98, the first diverter outlet 100, and the second diverter outlet 102, as described in greater detail below. The cam head 110 of the rotor portion 94 is disposed within the chamber 104 defined in the valve 92. Here, the shape of the cam head 110 and the chamber 104 limit rotation of the shaft 114 within the bore 106 of the valve 92 between a first configuration 94A (see FIGS. 12 and 13) and a second configuration 94B (see FIGS. 14 and 15). The selector pin 112 is radially offset from the shaft 114 and is shaped to engage the selector end 88 of the pushrod 82 of the slave 64. This arrangement translates linear movement of the pushrod 82 into rotational movement of the shaft 114. Thus, actuation of the master 62 affects movement of the valve 92 between the first and second configurations 94A, 94B (compare FIG. 12 with FIG. 14; compare FIG. 13 with FIG. 15). While the illustrated flow diverter 28 employs the valve 92 to effect selective control of the flow of bone cement BC from the diverter inlet 98 to either the first diverter outlet 100 or the second diverter outlet 102, other types of valves 92 and/or flow diverters 28 are contemplated. Moreover, it will be appreciated that the flow diverter 28 could be configured to control the flow of bone cement BC from the delivery device 22 to either the drool accumulator 38 or the delivery cannula 26 in a number of different ways, such as without a discrete valve 92.

As shown in FIG. 13, the first flow path 118 is defined between the diverter inlet 98 and the second diverter outlet 102 via the channel 116 when the valve 92 is in the first configuration. Put differently, when the user input mechanism 60 is in the released configuration 68B (see FIG. 7), the valve 92 is correspondingly positioned in the first configuration 94A such that bone cement BC flows out of the exit port 34 of the reservoir 30 into the drool accumulator 38 and does not flow towards the delivery cannula 26. Conversely, as shown in FIG. 15, the second flow path 120 is defined between the diverter inlet 98 and the first diverter outlet 100 via the channel 116 when the valve 92 is in the second configuration 94B. Put differently, when the user input mechanism 60 is in the engaged configuration 68B (see FIG. 8), the valve 92 is correspondingly positioned in the second configuration 94B such that bone cement BC flows out of the exit port 34 of the reservoir 30 into the delivery cannula 26 and does not flow towards the drool accumulator 38. It is also contemplated that the engaged configuration of the user input mechanism may correspond with the valve 92 being in the first configuration and the released configuration of the user input mechanism may correspond with the valve 92 being in the second configuration.

In operation, a user places the bone cement delivery system 20 such that the exit port of the delivery cannula 26 is disposed adjacent to the target site TS. In one exemplary embodiment, the valve 92 begins in the first configuration, establishing a fluid communication between the cement reservoir 30 and the drool volume of the drool accumulator 38, when the cement delivery input mechanism 41 is not actuated. Therefore, in order to deliver bone cement BC to the target site TS, the user must provide an input to the control surface to actuate the user input actuation mechanism 63, such as the trigger 68, to move the valve 92 to the second configuration, establishing a fluid communication between the cement reservoir 30 and the cannula coupler 25. However, it is also contemplated that actuation of the user input actuation mechanism 63 may correspond with the first configuration such that fluid communication between the cement reservoir 30 and the cannula coupler 25 is established without actuation of the user input actuation mechanism 63.

Once fluid communication is established between the cement reservoir 30 and the cannula coupler 25, the user engages the cement delivery input mechanism 41, for example, the twisting the knob, such that pressure is applied to the plunger 46 and the plunger 46 is moved within the cement reservoir 30 to displace the bone cement BC from the cement reservoir 30 through the exit port. In embodiments including the extension tube 24, such as the embodiments illustrated in FIGS. 1-6, the bone cement BC is displaced through the extension tube 24 towards the flow diverter 28. The fluid is then delivered through the valve 92 in the second configuration (see FIG. 15) to the target site TS. More specifically, the bone cement BC is displaced through the first diverter outlet of the flow diverter 28 to the cannula coupler 25 and out of the exit port of the delivery cannula 26.

Once the desired amount of bone cement BC has been delivered to the target site TS, the user changes the configuration of the valve 92 to the first configuration such that fluid communication is established between the cement reservoir 30 and the drool volume and fluid communication is interrupted between the cement reservoir 30 and the cannula coupler 25 (see FIG. 13). Changing the configuration of the valve 92 of the flow diverter 28 may be done by any of the methods described above including but not limited to engaging the trigger 68 to actuate the wire disposed between the trigger 68 and the valve 92 to move the valve 92 between configurations. Typically, the user also ceases pressure to the plunger 46 by disengaging the cement delivery input mechanism 41, such as the knob, around the same time as changing the configuration of the flow diverter 28, however, it is contemplated that cement delivery input mechanism 41 may continue to be actuated such that pressure to the plunger 46 may continue and additional bone cement BC is directed towards the drool accumulator 38. Moreover, even after the cement delivery input mechanism 41 is released, the bone cement BC disposed within the bone cement delivery system 20 is compressed and has a high potential energy. Because bone cement BC is a highly viscous and incorporates air therein, potential energy is necessarily stored in the bone cement BC as the plunger 46 of the delivery device 22 is advanced. Thus, under certain operating conditions, bone cement BC will continue to flow along and through the extension tube 24 and the delivery cannula 26 even after actuation of the cement delivery input mechanism has ceased. This latency is exacerbated by the flexibility and/or elastic expansion and contraction of certain components, such as the extension tube 24, during use. In other words, the initial pressure required to displace the bone cement BC remains elevated once movement of the plunger 46 has ceased. Therefore, additional, undesired bone cement BC continues flowing in the bone cement delivery system 20 after movement of the plunger 46 has stopped.

The flow diverter 28 affords the user with significant control over the flow of bone cement BC towards the target site TS during use while, at the same time, preventing residual bone cement in the extension tube 24, the reservoir 30, and/or the flow diverter 28 from flowing towards the delivery cannula 26 along the second flow path 120 by routing the residual bone cement along the first flow path 118 towards the drool accumulator 38. In particular, once the desired amount of bone cement BC has been delivered to the target site TS, the user changes the configuration of the flow diverter 28 to the first configuration (see FIG. 13) such that fluid communication is established between the cement reservoir 30 and the drool volume of the drool accumulator 38 and any residual bone cement will be displaced towards the drool accumulator 38 as described above. Moreover, in the first configuration of the valve 92, fluid communication is interrupted between the cement reservoir 30 and the cannula coupler 25 such that no residual bone cement from the extension tube 24 is delivered to the target site TS. Therefore, the residual bone cement and/or the pressure remaining in the residual bone cement may be collected in the drool accumulator 38 to prevent the pressurized residual bone cement from undesirably being delivered to the target site TS.

Additionally or alternatively, it is contemplated that the valve 92 of the flow diverter 28 may have an additional configuration (see FIG. 16) which establishes fluid communication between the drool accumulator 38 and the cannula coupler 25 and interrupts fluid communication between the cement reservoir 30 and the cannula coupler 25 and the drool accumulator 38 such that any residual bone cement between the valve 92 and the target site TS will move to the drool accumulator 38, and bone cement BC accumulated in the drool accumulator 38 can be displaced back through the flow diverter and into the cannula coupler 25 for delivery to the target site TS. Additionally, it is contemplated that this additional configuration may be established by a second flow diverter in the bone cement BC delivery system or as a separate embodiment of the bone cement BC delivery system, as described above.

While the bone cement delivery system 20 is depicted throughout the drawings and described herein with a single flow diverter 28, extension tube 24, delivery cannula 26, and drool accumulator 38, other arrangements are contemplated herein. Specifically, it is conceivable that a single delivery device 22 and a plurality of extension tubes 24 could be employed to direct bone cement BC to separate flow diverters 28 used to control flow towards respective delivery cannulas 26 and/or drool accumulators 38. Similarly, a single flow diverter 28 could be employed to control flow towards respective delivery cannulas 26. Moreover, the flow diverter 28 may be provided as a manifold configured to control flow towards delivery cannulas 26 and/or drool accumulators 38.

Several embodiments have been discussed in the foregoing description. However, the embodiments discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

The invention claimed is:

1. A system for deliverng bone cement through a delivery cannula, the system comprising:
    a cement reservoir;
    a flow diverter in fluid communication with the cement reservoir and comprising a valve defining a first diverter outlet and a second diverter outlet;
    a cannula coupler coupled to first diverter outlet of the flow diverter and configured to be coupled to the delivery cannula for directing the bone cement from the cement reservoir to the delivery cannula;
    a drool accumulator coupled to the second diverter outlet of the flow diverter and defining a drool volume for receiving the bone cement;
    a cement delivery input mechanism coupled to the cement reservoir and configured to be actuated to direct the bone cement from the cement reservoir towards the flow diverter; and
    a user input mechanism coupled to the flow diverter and configured to receive a user input to actuate the valve and establish the fluid communication selectively betveeri the cement reservoir and either the cannula coupler or the drool accumulator.

2. The system of claim 1, wherein the fluid communication is configured to be interrupted between the cement reservoir and the other one of the cannula coupler and the drool accumulator.

3. The system of claim 1, further comprising an actuator coupled to the drool accumulator and configured to be actuated to direct the bone cement received in the drool volume towards the flow diverter.

4. The system of claim 3, wherein the actuator is a plunger to form a syringe with the drool accumulator.

5. The system of claim 1, further comprising a hydraulic system comprising a slave cylinder coupled to the flow diverter, and a master cylinder coupled to the user input mechanism and in fluid communication with the slave cylinder.

6. The system of claim 1, further comprising a wire extending between and coupled to the user input mechanism and the valve.

7. The system of claim 1, further comprising a plunger disposed in the cement reservoir, a hydraulic pump coupled to the plunger, and the cement delivery input mechanism being configured to operate the hydraulic pump.

8. The system of claim 1, further comprising a flexible extension tube extending between and coupled to the cement reservoir and the flow diverter.

9. The system of claim 1, wherein the drool accumulator is at least partially formed from transparent material and comprises visual indicia indicative of the bone cement received in the drool volume.

10. The system of claim 1, wherein the user input mechanism is a trigger, and wherein the valve is configured to establish the fluid communication between the cement reservoir and the drool accumulator with the trigger in a released configuration, and establish the fluid communication between the cement reservoir and the cannula coupler with the trigger in an engaged configuration.

11. The system of claim 1, wherein the user input mechanism is a trigger, and wherein the valve is configured to establish the fluid communication between the cement reservoir and the drool accumulator with the trigger in an engaged configuration, and establish the fluid communication between the cement reservoir and the cannula coupler with the trigger in a released configuration.

12. A system for delivering bone cement through a delivery cannula, the system comprising:
 a cement reservoir;
 a flow diverter defining a diverter inlet in communication with the cement reservoir, a first diverter outlet, and a second diverter outlet, wherein the flow diverter comprises a valve;
 a cannula coupler coupled to the flow diverter and in fluid communication with the first diverter outlet; and
 a drool accumulator coupled to the flow diverter and defining a drool volume in fluid communication with the second diverter outlet,
 wherein the valve is configured to be actuated to establish the fluid communication between the cement reservoir and one of the cannula coupler and the drool accumulator.

13. The system of claim 12, wherein the fluid communication is configured to be interrupted between the cement reservoir and the other one of the cannula coupler and the drool accumulator.

14. The system of claim 12, further comprising a hydraulic system comprising a slave cylinder coupled to the valve, and a master cylinder in fluid communication with the slave cylinder and configured to hydraulically actuate the valve.

15. The system of claim 12, further comprising a trigger coupled to the valve, wherein the valve is configured to establish the fluid communication between the cement reservoir and the drool accumulator with the trigger in a released configuration, and establish the fluid communication between the cement reservoir and the cannula coupler with the trigger in an engaged configuration.

16. The system of claim 12, further comprising a trigger coupled to the valve, wherein the valve is configured to establish the fluid communication between the cement reservoir and the drool accumulator with the trigger in an engaged configuration, and establish the fluid communication between the cement reservoir and the cannula coupler with the trigger in a released configuration.

17. The system of claim 12, wherein the valve is a rotor.

18. A system for delivering bone cement through a delivery cannula, the system comprising:
 a cement reservoir;
 a flow diverter in fluid communication with the cement reservoir and comprising a valve;
 a cannula coupler coupled to the flow diverter and configured to be coupled to the delivery cannula for directing the bone cement from the cement reservoir to the delivery cannula;
 a drool accumulator in fluid communication with the flow diverter and defining a drool volume for receiving the bone cement;
 a user input mechanism coupled to the flow diverter and configured to receive a user input to actuate the valve and establish the fluid communication between the cement reservoir and one of the cannula coupler and the drool accumulator; and
 an actuator coupled to the drool accumulator and configured to be actuated to direct the bone cement received in the drool volume towards the flow diverter.

19. The system of claim 18, wherein the actuator is a plunger to form a syringe with the drool accumulator.

20. The system of claim 18, wherein the user input mechanism is further configured to receive another user input to further actuate the valve and establish the fluid communication between the cannula coupler and the drool accumulator, wherein actuation of the actuator is configured to direct the bone cement from the drool volume to the cannula coupler.

* * * * *